United States Patent [19]

Renga

[11] 4,384,115
[45] May 17, 1983

[54] PROCESS FOR PREPARING TETRAHYDRO-1,3-OXAZIN-2-ONES

[75] Inventor: James M. Renga, Midland, Mich.

[73] Assignee: The Dow Chemical Company, Midland, Mich.

[21] Appl. No.: 330,743

[22] Filed: Dec. 14, 1981

[51] Int. Cl.$^3$ ............................................. C07D 265/10
[52] U.S. Cl. ...................................................... 544/97
[58] Field of Search ........................................... 544/97

[56] References Cited

U.S. PATENT DOCUMENTS 2,940,971  6/1960  Lott ........................................ 544/97

FOREIGN PATENT DOCUMENTS 1626  7/1963  France.
35-11837  8/1960  Japan.

OTHER PUBLICATIONS

E. Testa, et al., Farmaco (Pavia) Ed. Sci., 13, 437–446 (1958), CA 53:6099a (at g) (1959).
Saul, S., et al., J. Am. Chem. Soc., 80, 4596–4599 (1958).

Primary Examiner—Richard Raymond
Attorney, Agent, or Firm—Douglas N. Deline

[57] ABSTRACT

Tetrahydro-1,3-oxazin-2-ones are prepared by contacting a 1,3-dioxan-2-one with an acyclic carbamate at a temperature from about 100° C. to about 250° C. in the presence of a catalytic amount of an alkali metal salt.

8 Claims, No Drawings

PROCESS FOR PREPARING TETRAHYDRO-1,3-OXAZIN-2-ONES

BACKGROUND OF THE INVENTION

The invention relates to tetrahydro-1,3-oxazin-2-ones. More particularly the invention concerns a new process for the formation of this known class of compounds.

Tetrahydro-1,3-oxazin-2-ones are known compounds that demonstrate utility as drugs for stimulation of the central nervous system and as barbituate antagonists, as disclosed by E. Testa et al. in *Farmaco (Pavia) Ed. Sci.*, 13, 437 (1958) (CA 53:6099) and by Krewel Lueffer G.m.b.h., French patent M 1626 (CA 58:12576) which teaching is incorporated herein by reference. The compounds are also useful intermediates in the preparation of additional pharmaceuticals having psychotropic utility.

In the past, several methods have been disclosed for the preparation of tetrahydro-1,3-oxazin-2-ones and substituted derivatives thereof. Suitable methods have involved the reaction of 1,3-propanolamine with a reactive carbonyl-containing compounds such as phosgene (USP 2,940,971), ethylchloroformate (Berichte, 65B, 385 (1932)), or diethyl carbonate (French patent M 1626, CA 58:12576).

In addition, tetrahydro-1,3-oxazin-2-ones have been prepared by the reaction of 1,3-halopropanols with potassium cyanate in a polar solvent such as N,N-dimethylformamide (Japanese Kokai 11,837 (1960)).

It is also known to prepare N-phenyl-substituted tetrahydro-1,3-oxazin-2-ones by the reaction of phenyl isocyanate with a 1,3-dioxan-2-one in the presence of a catalytic amount of lithium chloride catalyst.

SUMMARY OF THE INVENTION

According to the present invention tetrahydro-1,3-oxazin-2-ones corresponding to the formula:

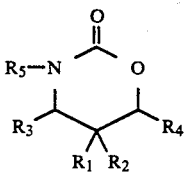

are prepared by reacting a 1,3-dioxan-2-one corresponding to the formula:

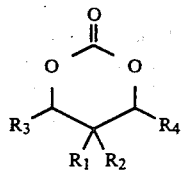

with an acyclic carbamate corresponding to the formula $R_5HNC(O)OR_6$, and thereafter separating the resulting by-products, carbon dioxide and $R_6OH$.

In the above formulas, $R_1$–$R_4$ are hydrogen, alkyl or aryl of up to about 10 carbons, $R_5$ is alkyl or aryl of up to about 10 carbons and $R_6$ is lower alkyl or haloalkyl.

Preferred according to the invention are those reactants wherein $R_1$ and $R_2$ are hydrogen or lower alkyl, $R_3$ and $R_4$ are hydrogen, $R_5$ is lower alkyl or phenyl and $R_6$ is methyl or ethyl.

Most preferably, $R_1$ and $R_2$ are methyl or ethyl and $R_5$ is phenyl.

The 1,3-dioxan-2-one and the acyclic carbamate reactants are known and commmercially available or they may be prepared by known methods from readily available starting materials. A particularly suitable process for preparing the 1,3-dioxan-2-one reactant is by transesterification of a suitable 1,3-propane diol with, e.g., diethyl carbonate, under transesterification conditions. The process conditions are known, having been previously described by S. Saul et al., *J. Am. Chem. Soc.*, 80, 4596–4599 (1958), and by others. The carbonate reactant may suitably be prepared by reaction of a suitable primary amine of the formula $R_5NH_2$ with a diorgano carbonate having the formula $R_6OC(O)OR_7$, where $R_7$ is lower alkyl or halo alkyl and preferably chosen to be the same as $R_6$ thereby simplifying separation of the products formed. The desired product $R_5NHC(O)OR_6$ is recovered and separated from by-product alcohol.

DETAILED DESCRIPTION OF THE INVENTION

The 1,3-dioxan-2-one reactant described above and the acyclic carbamate are reacted by bringing the two compounds into contact at an elevated temperature. Suitable reaction temperatures are from about 100° C. to about 250° C. and preferably from about 150° C. to about 200° C. Reaction times may vary from short contact times on the order of several minutes to as long as several hours depending on the reactants and temperatures employed. Agitation as by stirring or introduction of turbulent flow conditions may be employed as an aid in contacting the reactants.

The reaction may be carried out at any pressure. Preferred are pressures suitably chosen to permit distillative removal of the by-product $R_6OH$. Where $R_6OH$ is particularly high boiling, a reduced pressure may be employed. A sweep stream of an inert gas may also be employed to help remove volatile reaction by-products. Suitable inert gases include nitrogen or carbon dioxide.

Generally, where the reactants are liquids at the reaction temperatures employed, a solvent need not be employed for the reaction. However, where desired a solvent may be employed such as when solid, high molecular weight carbamate reactants are employed. Suitable solvents are inert liquids having boiling points higher than the reaction temperatures employed. Preferred solvents include sulfolane, nitrobenzene and pyrrolidone.

A catalytic amount of an alkali metal salt is employed in order to increase the rate of reaction. Suitable alkali metal salts include alkali metal carbonates or halides. Preferred are potassium or lithium carbonates, chlorides or fluorides. Particularly preferred is potassium carbonate. The catalyst is ordinarily employed in combination with a suitable phase-transfer catalyst such as cyclic polyalkylene oxides such as crown ethers. A preferred phase-transfer catalyst is 18-crown-6.

The product is recovered merely by cooling the reaction mixture. Where a solvent has been employed, the product may be recovered by distillation of the solvent.

The process may be employed in a batch or alternatively a continuous process.

SPECIFIC EMBODIMENTS OF THE INVENTION

Having described the invention, the following examples are provided as further instructive and are not to be construed as limiting the invention.

EXAMPLE 1

Tetrahydro-3-benzyl-5,5-dimethyl-1,3-oxazin-2-one

In a glass reaction vessel, 5,5-dimethyl-1,3-dioxan-2-one (13.0 g, 0.1 mole), ethyl-N-benzyl carbamate (17.9 g, 0.1 mole), potassium carbonate (0.134 g, 0.001 mole) and 18-crown-6 (0.26 g, 0.001 mole) were combined and heated to 180° C. while removing ethanol by distillation. After heating for four hours, evolution of carbon dioxide ceased and a total of 4.6 g of ethanol were collected.

The reaction mixture was cooled and the remaining solid recrystallized from 200 ml of a 50:50 mixture of ether and pentane. The product, tetrahydro-3-benzyl-5,5-dimethyl-1,3-oxazin-2-one, was identified by nuclear magnetic resonance spectroscopy. Yield: 18.0 g, 82 percent; m.p. 74° C.-75° C.

EXAMPLES 2-7

The reaction conditions of Example 1 were substantially repeated. Accordingly, the 1,3-dioxan-2-one and carbamate reactants further identified in Table I were reacted thereby preparing the desired product which was identified by nuclear magnetic resonance spectroscopy.

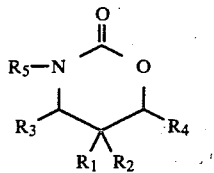

wherein $R_1$–$R_4$ independently are hydrogen, alkyl or aryl of up to about 10 carbons and $R_5$ is alkyl or aryl of up to about 10 carbons, comprising contacting a 1,3-dioxan-2-one corresponding to the formula:

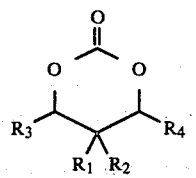

wherein $R_1$–$R_4$ are as previously defined, with an acyclic carbamate corresponding to the formula $R_5HNC(O)OR_6$, wherein $R_5$ is as previously defined and $R_6$ is lower alkyl or haloalkyl, in the presence of a catalytic amount of an alkali metal salt at a temperature from about 100° C. to about 250° C. for a time sufficient to produce the desired tetrahydro-1,3-oxazin-2-one.

2. The process of claim 1 wherein the temperature is from about 150° C. to about 200° C.

3. The process of claim 1 wherein the reaction mix-

TABLE I

| Example | Reactant I | Reactant II | Product | Temp (°C.) | Time (hr) | % Yield |
|---|---|---|---|---|---|---|
| 2 | 5,5-dimethyl-1,3-dioxan-2-one | ethyl-N—methyl carbamate | tetrahydro-3-methyl-5,5-dimethyl-1,3-oxazin-2-one | 190 | 6 | 71 |
| 3 | 5,5-dimethyl-1,3-dioxan-2-one | ethyl-N—ethyl carbamate | tetrahydro-3-ethyl-5,5-dimethyl-1,3-oxazin-2-one | 190 | 6 | 79 |
| 4 | 5,5-dimethyl-1,3-dioxan-2-one | methyl-N—benzyl carbamate | tetrahydro-3-benzyl-5,5-dimethyl-1,3-oxazin-2-one | 190 | 4 | 36 |
| 5 | 5,5-dimethyl-1,3-dioxan-2-one | ethyl-N—phenyl carbamate | tetrahydro-3-phenyl-5,5-dimethyl-1,3-oxazin-2-one | 180 | 1 | 84 |
| 6 | 1,3-dioxan-2-one | ethyl-N—ethyl carbamate | tetrahydro-3-ethyl-1,3-oxazin-2-one | 180 | 2 | 44 | ture additionally comprises a phase-transfer catalyst.

4. The process of claim 3 wherein the phase-transfer catalyst is a crown ether.

5. The process of claim 4 wherein the crown ether is 18-crown-6.

6. The process of claim 1 wherein the reaction mixture additionally comprises an inert liquid solvent having a boiling point above the reaction temperature.

7. The process of claim 6 wherein the solvent is sulfolane, nitrobenzene, or pyrrolidone.

8. The process of claim 1 wherein 5,5-dimethyl-1,3-dioxan-2-one is contacted with ethyl-N-benzyl carbamate to prepare tetrahydro-3-benzyl-5,5-dimethyl-1,3-oxazin-2-one.

What is claimed is:

1. A process for preparing tetrahydro-1,3-oxazin-2-ones corresponding to the formula:

* * * * *